United States Patent [19]
Dong et al.

[11] Patent Number: 5,980,890
[45] Date of Patent: Nov. 9, 1999

[54] **PURIFICATION AND CHARACTERIZATION OF ALKALINE PHOSPHATES FROM *THERMOTOGA NEAPOLITANA***

[75] Inventors: Guoqiang Dong, Winnipeg, Canada; Joseph G. Zeikus, Okemos, Mich.

[73] Assignee: Michigan State University, Lansing, Mich.

[21] Appl. No.: 08/806,138

[22] Filed: Feb. 25, 1997

Related U.S. Application Data

[60] Provisional application No. 60/012,315, Feb. 26, 1996.

[51] Int. Cl.$^6$ ..................................................... A61K 38/46
[52] U.S. Cl. ........................................... 424/94.6; 435/196
[58] Field of Search ............................ 424/94.6; 435/196

[56] References Cited

U.S. PATENT DOCUMENTS

| | | | |
|---|---|---|---|
| 4,030,995 | 6/1977 | Starkweather | 204/180 |
| 4,656,128 | 4/1987 | Chlebowski et al. | 435/7 |
| 4,659,666 | 4/1987 | May et al. | 435/188 |
| 4,720,458 | 1/1988 | Sullivan et al. | 435/196 |
| 5,264,098 | 11/1993 | Chevigné | 204/182.8 |

OTHER PUBLICATIONS

Bradford, Marion M., "A Rapid and Sensitive Method for the Quantitation of Microgram Quantities of Protein Utilizing the Principle of Protein–Dye Binding", *Analytical Biochemistry*, 72: 248–254 (1976).

Coolbear, et al., "The Enzymes from Extreme Thermophiles," *Advances in Biochemical Engineering Biotechnology*, 45:77–78 (1992).

Dorn, Gordon L., "Purification and Characterization of Phosphatase I from *Aspergillus nidulans*", *J. Biol. Chem.*, 243 No. 12: 3500–3506 (1968).

Fernley, H. N., "Mammalian Alkaline Phospatases", *The Enzymes*, Academic Press, New York vol. IV: 417–447 (1971).

Garen, et al., "A Fine–Structure Genetic and Chemical Study of the Enzyme Alkaline Phosphatase of *E. coli*", *Biochem. Biophys. Acta*, 38:470–483 (1960).

Glenn, et al., "Sporulation in *Bacillus subtilis* 168; Comparison of Alkaline Phosphatase from Sporulating and Vegetative Cells", *Biochem. J.*, 123: 129–138 (1971).

Glew, et al., "Studies on the Extracellular Alkaline Phosphatase of *Micrococcus sodonensis*", *J. Biol. Chem.*, 246: 1566–1574 (1971).

Gottesman, et al., "Kinetic Properties of Cobalt Alkaline Phosphatase", *Biochemistry*, 8 No. 9: 3776–3783 (1969).

Hartog, et al., "An Alkaline Phosphatase from Thermus sp Strain Rt41A," *Int. J. Biochem.*, 24(10):1657–1660 (1992).

Jablonski, et al., "Preparation of Oligodeoxynucleotide–Alkaline Phosphatase conjugates and Their Use as Hybridization Probes", *Nucleic Acid Research*, 14 No. 15:6115–6128 (1986).

Janeway et al., "Magnesium in the Active Site of *Escherichia coli* Alkaline Phosphatase is Important for Both Structural Stabilization and Catalysis", *Biochemistry*, 32: 1601–1609 (1993).

Jannasch, et al., "*Thermotoga neapolitana* sp. nov. of the extremely thermophilic, eubacterial genus Thermotoga," *Arch. Microbiol.*, 150:103–104 (1988).

Kim, et al., "Reaction Mechanism of Alkaline Phosphatase Based on Crystal Structures: Two–metal Ion Catalysis", *J. Mol. Biol.*, 218: 449–464 (1991).

Laemmli, et al., "Cleavage of Structural Proteins During the Assembly of the Head of Bacteriophage T4", *Nature*, 227: 680–685 (1970).

McComb, et al., "Alkaline Phosphatase", Plenum Press, New York, 27–51; 525–526; 206–207 (1979).

Say, et al., "Alkaline Phosphatase from Rat Osseous Plates: Purification and Biochemical Characterization of a Soluble Form", *Biochimica et Biophysica Acta*, 1074: 256–262 (1991).

Spencer, et al., "Effect of Colbalt on Synthesis and Activation of *Bacillus licheniformis* Alkaline Phosphatase", *J. Bacteriology*, 145 No. 2:926–933 (1981).

Vallee, et al., "New Perspective on Zinc biochemistry: Cocatalytic Site in Multi–Zinc Enzymes", *Biochemistry*, 32 No. 26, 6493–6495 (1993).

Wachsmuth, et al., "Alkaline Phosphatase from Pig Kidney", *Biochem. J.*, 141:273–282 (1974).

Yasuura, et al., "Partial Purification of Alkaline Phosphatase form Bovine Polymorphonuclear Neutrophils and Some Properties", *Comp. Biochem. Physiol.* 82B No. 4: 587–593 (1985).

Yasuura, et al., "Characterization of Alkaline Phosphatase from Bovine Polymorphonuclear Neutrophils", *Comp. Biochem. Physiol.* 82B No. 4: 595–598 (1985).

*Primary Examiner*—Jean C. Witz

[57] ABSTRACT

This invention relates in general to alkaline phosphatase and, in particular, to alkaline phosphatase from a hyperthermophilic microorganism. The invention also relates to a method of purifying a hyperthermophilic alkaline phosphatase.

7 Claims, 5 Drawing Sheets

PURIFICATION AND CHARACTERIZATION OF ALKALINE PHOSPHATES FROM *THERMOTOGA NEAPOLITANA*

CROSS-REFERENCE TO RELATED APPLICATIONS

This application claims the benefit of U.S. Provisional Application No. 60/012,315, filed Feb. 26, 1996.

STATEMENT REGARDING FEDERALLY SPONSORED RESEARCH OR DEVELOPMENT

This material is based upon work supported by the Cooperative State Research, Education, and Extension Service, U.S. Department of Agriculture, under Agreement No. 94-34189-0067.

FIELD OF THE INVENTION

The present invention relates, in general, to alkaline phosphatase, and in particular to alkaline phosphatase from a hyperthermophilic microorganism. The invention also relates to a method of purifying a hyperthermophilic alkaline phosphatase.

BACKGROUND OF THE INVENTION

The importance of alkaline phosphatase (orthophosphoric-monoester phosphohydrolase EC 3.1.3.1) in clinical medicine and molecular biology has made it a popular subject for scientific study and commercial utility. (See for example, H. N. Ferley, "The Enzymes," Academic Press, New York Vol. IV, pp. 417–447, (1971); R. B. McComb, et al., "Alkaline Phosphatase," Plenum Press, New York (1979); B. L. Vallee and D. S. Auld, *Biochem.* 32:6494–6500 (1993)).

Alkaline phosphatase has been purified and characterized from a variety of bacterial, fungal, alga, invertebrate and vertebrate species (R. B. McComb et al., supra). The enzyme also has been purified from mesophiles and thermophiles. A relatively unstable alkaline phosphatase was characterized from a thermophilic Thermus species. (A. T. Hartog et al. *Int. J. Biochem.*, 24, 1657–1660 (1992), but alkaline phosphatase has not, until now, been purified and characterized from a hyperthermophile.

Hyperthermophiles are a group of microorganisms which grow at 80° C. or above. Extremely thermostable enzymes produced by these organisms have attracted increased attention because they allow structural and functional studies of proteins at very high temperatures and have many molecular biology-related, and potential industrial, applications. (See for example, M. W. W. Adams *Annu. Rev. Microbiol.* 47:627–658 (1993)); T. Coolbear et al. *Adv. Biochem. Eng./Biotechol.* 45:57–98 (1992)). The enzymes from hyperthermophilic microorganisms also provide opportunities to investigate the structure and function of proteins at very high temperatures.

Thermotoga is a hyperthermophilic eubacterium that grows optimally at 80° C. and is the most thermophilic eubacterium discovered to date. (H. W. Jannasch et al., *Arch Microbiol.* 150:103–104, (1988)).

The present invention provides alkaline phosphatase from *Thermatoga neapolitana* in purified form and a method of effecting that purification.

BRIEF SUMMARY OF THE INVENTION

This invention relates to our isolation and characterization of a new thermostable alkaline phosphatase isolated from a hyperthermophilic eubacterium of the genus Thermotoga, and a process for purification of that alkaline phosphatase.

We have discovered that the alkaline phosphatase isolated from *Thermotoga neapolitana* ("*T. neapolitana*") is more thermostable than any previously known alkaline phosphatase. It was found to have both a high optimal reaction temperature and a high optimal pH.

The alkaline phosphatase was isolated and purified from *T. neapolitana* (DSM 5068) and was purified 2880 fold with 44.3% yield. and a specific activity of 663 U/mg of protein at 60° C. The purified enzyme showed a single protein band of Mr 45,000 on Sodium dodecyl sulphate-polyacrylamide gel electrophoresis (SDS-PAGE) and an apparent molecular weight of 87,000 estimated by gel filtration chromatography, suggesting a homogenous dimer structure. The optimal pH and temperature of the enzyme were 9.9 and 85° C. respectively.

The method used to purify the alkaline phosphatase of the invention comprises, as a first step, the preparation of a crude hyperthermophilic eubacteria cell extract. The cell extract is then subjected to heat treatment in the presence of $CO^{2+}$ and ammonium sulfate precipitation. The resuspended enzyme is then subjected to a combination of ion exchange and affinity chromatographies.

It is a general object of the present invention to provide hyperthermophilic alkaline phosphatase in pure form.

It is another object of the invention to provide a method for purifying hyperthermophilic alkaline phosphatase.

It is a further object of the invention to provide hyperthermophilic alkaline phosphatase isolated from a hyperthermophilic eubacterium, and in particular from the hyperthermophile *T. neapolitana*.

It is an advantage of the present invention that this new hyperthermophilic alkaline phosphatase provides the opportunity to investigate the structure and function of proteins at very high temperatures.

It is a further advantage of the present invention that the hyperthermostable alkaline phosphatase of the present invention is more robust and better able to withstand transportation and storage intact than alkaline phosphatase from non-hyperthermophilic microorganisms.

It is another advantage of this invention that the hyperthermophilic alkaline phosphatase will be useful in ELISA systems, non-isotopic detection/probing systems, non-radioactive hybridization and sequencing procedures, and other molecular biology applications which require alkaline phosphatase having both high thermostability and high specific activity.

Further objects and advantages of the invention will be apparent to those skilled in the art after review of the specification, claims and figures presented herein.

DETAILED DESCRIPTION OF THE INVENTION

Figure 1:
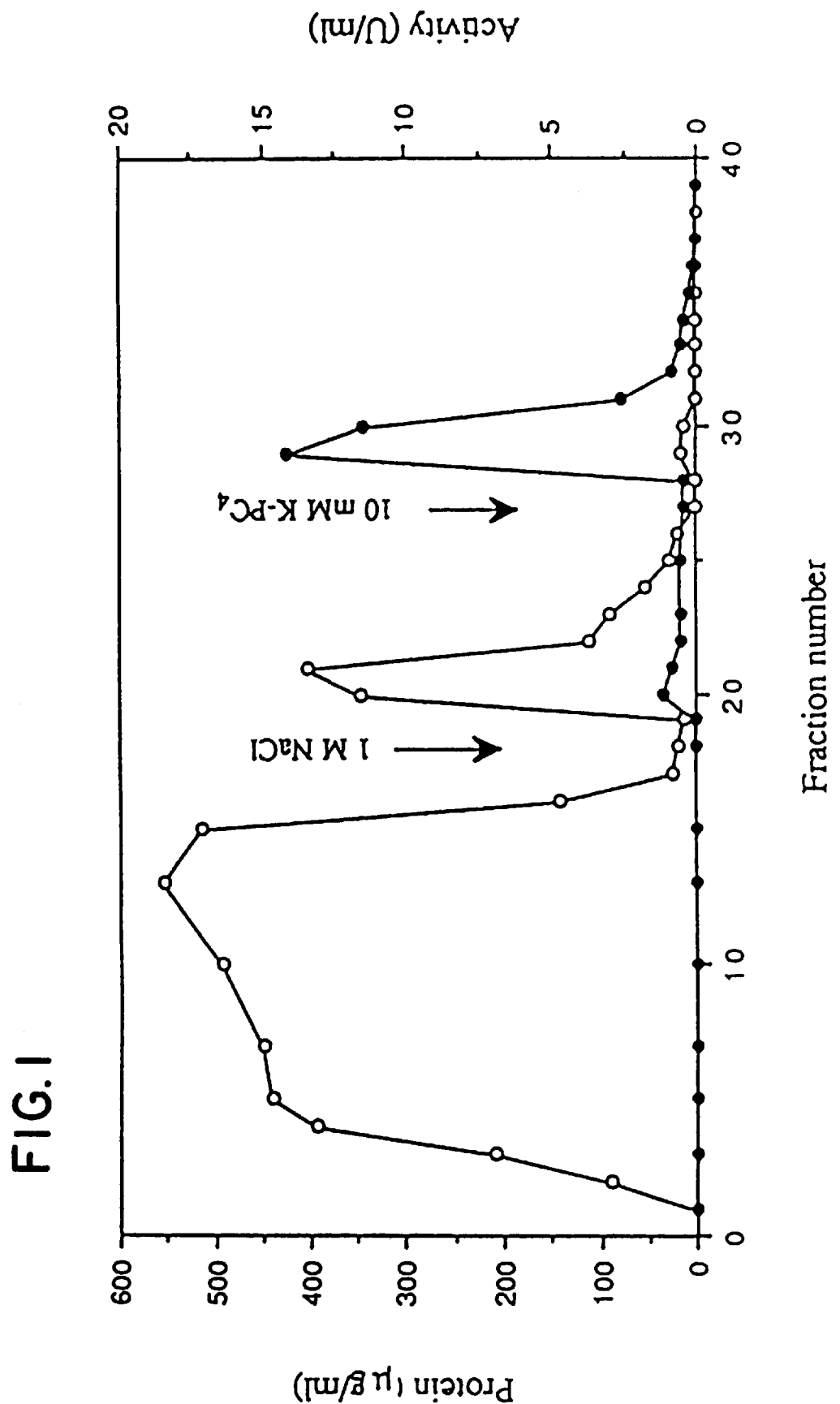
FIG. 1 is a chromatographic pattern of protein (○) and *T. neapolitana* alkaline phosphatase activity (●) on the histidyldiabenzylpropionic acid-Agarose column. The arrows indicate the places where reagents were added and pulse elutions were performed.

The present invention relates, in general, to isolation, purification, and characterization of hyperthermophilic alkaline phosphatase and a process for purifying the same from a eubacteria, specifically, *T. neapolitana*.

Alkaline phosphatase of *T. neapolitana* is the first alkaline phosphatase isolated and purified from a hyperthermophilic microorganism. Among all alkaline phosphatases reported, *T. neapolitana* alkaline phosphatase is the most thermostable (See Table 2, infra). The enzyme had extremely high optimal temperature and pH values. Under optimal condition, *T. neapolitana* alkaline phosphatase displayed 30% higher activity than calf intestine alkaline phosphatase did with p-nitrophenyl-phosphate as a substrate.

In a preferred embodiment, this novel, hyperthermophilic alkaline phosphatase has the following physical and chemical properties:

(1) Molecular weight: approximately 87,000;
(2) Activator: $Co^{2+}$;
(3) Inhibitors: ethylene diamine tetraacetic acid (EDTA), $Ni^{2+}$ and $Cu^{2+}$;
(4) optimum temperature: 85° C.;
(5) pH stability at room temperature: 5.0–11.5 (for residual activity equal or above 95%);
(6) pH optimum: 9.9;
(7) $K_m$ and $V_{max}$ values of 183 μM and 1352 U/mg respectively.

The native molecular weight is comparable with most microbial alkaline phosphatases (MW 68,000–120,000) but is lower than that of mammalian enzymes (MW 120,000–200,000).

The optimal temperature of *T. neapolitana* alkaline phosphatase activity corresponds to the growth temperature of the bacterium. The optimal pH of the enzyme activity is 9.9, which is higher than most reported alkaline phosphatases, whose optimal pH values are approximately 8.5–9.5. (R. B. McComb et al., supra).

Like other alkaline phosphatases reported, *T. neapolitana* alkaline phosphatase is a metalloenzyme. Its activity was reduced nearly to zero in the presence of a chelating agent. After extensive dialysis, less than 5% of the original activity remained, which implied that some metal ion remained on the protein due to strong binding. About 90% of the apoenzyme activity can be restored by the addition of $Zn^{2+}$, $Mg^{2+}$, or $Mn^{2+}$, indicating that the enzyme structure is quite stable even when the metal ions are removed. Some apo-alkaline phosphatase activities, such as *Bacillus licheniformis* cannot be restored by the addition of metal ions, (Spencer et al., *J. Bacteriol.*, 145:926–933 (1981)).

One striking property of *T. neapolitana* alkaline phosphatase is that unlike other alkaline phosphatases examined, $Co^{2+}$ enhances both enzyme activity and thermostability. This differs dramatically from most other reported alkaline phosphatases in which zinc and/or magnesium ions generally are an integral part of alkaline phosphatase and are essential for its activity and conformation structure. (See for example, C. M. Janeway et al., *Biochem.* 32:1601–1609 (1993), and E. E. Kim et al., *J. Mol. Biol.*, 218:449–464 (1991), discussing *E. coli*.) Few native alkaline phosphatases have been found to include native metal ions other than zinc or magnesium. (See R. H. Glew et al., *J. Biol. Chem.* 246:1566–1574 (1971) (identifying an exception in *Micrococcus sodonesis*)). Cobalt can replace zinc and magnesium in the *E. Coli* apoenzyme, but only 12% of the alkaline phosphatase activity is restored. (Gottesman et al., *Biochem.*, 8:3776–3782 (1969).

The method used to purify the alkaline phosphatase of the invention comprises, as a first step, the preparation of a crude hyperthermophilic eubacteria cell extract. The cell extract is then subjected to heat treatment in the presence of $CO^{2+}$ and ammonium sulfate precipitation. The resuspended enzyme is then subjected to a combination of ion exchange and affinity chromatographies.

The purified alkaline phosphatase of the present invention has numerous applications. During the last two decades, alkaline phosphatase has found wide application in detection systems such as enzyme-linked immunoassay (ELISA) systems, non-isotopic probing, blotting and sequencing procedures. (See M. M. Manson, "Immunochemical Protocols," Humana Press, New Jersey (1992); E. Jablonski et al., *Nucleic Acids Res.* 14:6115–6128 (1986)).

Most detection applications require a form of alkaline phosphatase which has a high specific activity for high detection sensitivity as well as enzyme thermostablilty for long shelf life. Thermostable enzymes, such as the alkaline phosphatase of the present invention, not only are stable at high temperatures, but they also usually are more stable than their mesophilic counterparts even at room temperature.

Recently, the need for a thermostable alkaline phosphatase with high activity has been recognized for additional applications, including, for example, reduced chemical denaturation during preparation of enzyme-probe conjugates, longer half lives of immobilized enzymes in biosensors, and, reuse of enzymes in various detection systems.

Additionally, because of the high activity and thermostability of the present alkaline phosphatase, it can be used as a starting enzyme for future genetic studies aimed at designing a factitious enzyme that is extremely stable but displays optimal activity at around 40° C.

Commercial alkaline phosphatase from calf intestine currently is widely used in molecular biology and other applications because of its high specific activity. However, the usefulness of calf intestine alkaline phosphatase is limited by its inherently low thermostability and shelf life. The thermostability and high specific activity of the alkaline phosphatase of the present invention renders this enzyme ideally suitable for molecular biological applications requiring high specificity and thermostability and make this enzyme an attractive alternative to calf intestine alkaline phosphatase.

The following non-limiting Examples describe certain aspects of the invention in greater detail.

EXAMPLES

The following experimental details are referenced in the specific Examples that follow:

Materials and Methods

Chemicals.

DEAE-Sepharose Sephacryl S 200 and Phenyle-Sepharose were purchased from Pharmocia Fine Chemica AB, Uppsala, Sweden. Histidyldiazobenzylpropionic acid-Agarose, p-nitrophenyl-phosphate, adenosine-5'-diphosphate disodium salt (ADP), adenosine-5'-triphosphate disodium salt (ATP), β-glycerol-phosphate, D-glucose-1-phosphate, D-glucose-6-phosphate, D-fructose-6-phosphate, D-fructose-1, 6-diphosphate and Triton X-100 from Sigma, Chemical Co., U. S. A. Ethylenediamine tetraacetic acid disodium salt (EDTA) and alkaline phosphatase (calf intestine) from Boehringer Mannheim GmbH, Germany. Others chemicals were from standard sources.

Bacterium and culture condition.

The cultures of *T. neapolitana* used in the studies described herein employed strain DSM 5068, originally obtained from Deutsche Sammlung von Mikroorganismen, Braunschweig, Germany. *T. neapolitana* (DSM 5068) was cultured in a medium contained per liter: 4 g starch, 2 g yeast extract, 3 g tryptone, 1 g glucose, 15 g NaCl, 0.35 g KCl, 2.7 g $MgCl_2$ $6H_2O$, 0.1 g $NaHCO_3$, 0.14 g $CaCl_2$ $2H_2O$, 0.05 g $K_2HPO_4$, 15 mg $H_3BO_3$, 20 mg KBr, 15 mg $Fe(NH_4)_2(SO_4)_2$, 3 mg $Na_2WO_4$ $2H_2O$, 6 mgKI, 0.6 mg NiCl $6H_2O$, 1 g S°, 1 mg resazurin, 4 g starch, 2 yeast extract, 3 g trypton, 1 g glucose. The initial pH was adjusted to 7.5 with 1 M NaOH. Glucose and phosphate were autoclaved separately. Inocula were routinely grown in a closed bottle (700 ml medium in 1.5 L volume bottle) overnight at 80° C. and anaerobic condition was attained by heating the medium and sparging with nitrogen gas before autoclaved. Large scale was carried out in a fermenter (B. Brann Biotech, Bethlehem, Pa., U. S. A.) containing 10 L medium. The fermentation temperature was maintained at 80° C. under nitrogen sparge with gentle stirring (100 rpm). After about 20 h incubation, cells were harvested with Millipore Pellicon Cassette Cell Harvester (Bedford, Mass., U.S.A.). The further concentration was done by centrifugation at 16,300× g, 15 min and the cell pellet was stored at −20° C.

Purification of alkaline phosphatase.

All the procedures were performed under room temperature and aerobic condition unless otherwise stated.

1. Preparation of cell extract: Frozen cells (40 g wet mass) were suspended in 100 ml of 50 mM Tris-HCl buffer at pH 7.5 ("Buffer A") containing 0.15% (w/v) Triton X-100 and stirred for 1 h. After centrifugation at 16,300×g for 15 min, the pellet was extracted once more by repeating above procedure. The supernatants were pooled together and used as the crude enzyme preparation.

2. Heat treatment and $(NH_4)_2SO_4$ precipitation: 40 mM $CoCl_2$ was added to the cell extract and the solution was heated for 20 min in a 100° C. water bath and then quickly cooled in a room temperature water bath. After centrifugation, the precipitate was discarded and 65% saturation $(NH_4)_2SO_4$ was added to the soluble fraction. The pellet by ammonia sulfate precipitation was harvested by centrifugation and then suspended in 50 mM Tris-HCl buffer at pH 7.5 and dialyzed extensively against the same buffer at cool room.

3. Ion-exchange chromatography: The dialyzed enzyme (25 ml) from above treatment was applied to DEAE-Sepharose column (2.6 cm×15 cm) equilibrated with Buffer A. The enzyme was eluted by applying a linear gradient of 0.0–0.4 M KCl in Buffer A at a flow rate of 10 ml/tube/10 min. The alkaline phosphatase activity was detected early in the elution.

4. Affinity chromatography: The active fractions from an ion-exchange column were pooled and loaded into histidyl-diazobenzylpropionic acid-Agarose column (1.0×6 cm) equilibrated with Buffer A. After washing, the nonspecific bound proteins were eluted with 1 M NaCl in the Buffer A. Finally, the enzyme was eluted by pulse elution with 10 mM sodium phosphate in Buffer A (FIG. 1).

Molecular Mass Determination.

A 0.5×45 cm column containing Sephacryl S 200 was balanced with Buffer A containing 0.2 M NaCl. Marker proteins included horse heart cytochrome C (12,400), carbonic anhydrase (29,000), bovine serum albumin (66,000), alcohol dehydrogenase (150,000) and Blue Dextran (200,000). The purified sample were applied to the column in the presence of Buffer A. The flow rate was 7 ml/h. Elution of the marker proteins and of the native alkaline phosphatase were determined by 280 nm UV-detector and activity assay.

Sodium dodecyl sulphate-polyacrylamide gel electrophoresis (SDS-PAGE) with 12% polyacrylamide gel was performed according to the procedure by Laemmli (U. K. Laemmli, *Nature*, 227:680–685 (1970)) using a BioRad mini Protein II electrophoresis unit and standard molecular weight markers (BioRad Laboratories Ltd., Richmond, Calif., USA). The protein bands were made visible by staining with Commassie Brilliant blue R-250.

Protein determination.

Protein concentration were determined using Bio-Rad solution (Sigma, U.S.A.) with bovine serum albumin as the standard protein. (M. M. Bradford, *Anal. Biochem.*, 72:248–254 (1976)).

Enzyme Assay.

Alkaline phosphatase activity was assayed by following the release of p-nitrophenol from p-nitrophenyl phosphate. The reaction was initiated by the addition of 50 μl enzyme with appropriate dilution into a cuvette containing 1 ml of 0.2 M Tris buffer (pH 9.9 at 60° C.) and 50 μl of 24 mM p-nitrophenyl phosphate at 60° C. The initial linear change in the absorbance at 410 nm was detected by recording spectrophotometer (Cary 219, U.S.A.), thermostated at 60° C. One enzyme activity unit represents the hydrolysis of 1 μl mole of substrate per min under these standard assay condition.

The optimal pH for the enzyme activity was measured using 0.2 M Tris-HCl buffer at different pH values and a temperature of 60° C. All the pH values of these buffers were measured at room temperature and corrected for pH change at high temperature using $\Delta pka/\Delta T°C$ for Tris. (See D. D. Perrin and B. Dempsey "Buffers for pH and Metal Ion Control," Chapman & Hall, London, 157–163 (1974)). To determine the temperature of maximal activity, activity assays were performed in 0.2 M Tris-HCl at different temperatures. Because there was a small amount of nonenzymatic hydrolysis at higher temperature, a control without enzyme also was examined.

When phosphate esters other than p-nitrophenyl phosphate were used as substrates, phosphatase activity was determined by measuring the amount of phosphate liberated during 10 min incubation at 80° C. The incubation mixture containing: 0.1 ml of 0.1 M different substrates, 0.1 ml pure enzyme and 0.2 M Tris containing 5 mM $CoCl_2$ and 5 mM MgCl$_2$ in a total volume of 1 ml. Controls for non-enzymatic hydrolyzation on each substrate were performed. Samples were assayed for inorganic phosphate released by a modified method (J. F. Robyt and B. J. White, "Biochemical Techniques: Theory and Practice," Brooks Cole, Monterey Calif. (1987)). As a comparison, a commercial alkaline phosphatase from calf intestine was also used to hydrolyze these phosphate esters. Reaction conditions were 0.1 M Tris-HCl buffer (pH 8.5) containing 50 mM MgCl$_2$ and 5 mM ZnCl$_2$ at 38° C. Other reaction condition was the same as above.

Thermal Inactivation Studies.

100 μl PCR crew cap tubes (cat. #72.733.050, sarstedt; Newton, N.C.) containing 20 μg purified enzyme and 5 mM Co$^{2+}$ or 5 mM Mg$^{2+}$ in 100 μl Buffer A were incubated in water bathes at different temperature for varying periods. Following the treatment, the samples were quickly cooled in a water bath at room temperature and the residual activities were assayed under standard condition.

EDTA and Metal Ion Treatment.

The purified alkaline phosphatase in Buffer A was incubated at room temperature for 1 h in the presence of EDTA at 0.0–5.0 mM concentration respectively. The residual enzyme activity was assayed under standard conditions.

For metal ion treatment, 10 mM EDTA was added into a tube containing the purified alkaline phosphatase in Buffer A. After 1 h, the mixture was dialyzed against Buffer A containing 2 mM EDTA and then three times against Buffer A without EDTA. Subsequently, 2 mM of different metal ions were added to the deionized enzyme solutions, and the mixtures were incubated for 1 h at room temperature. For a comparison, 2 mM of various metal ions were added directly to purified protein and incubated under the same conditions. All the metal ions used were in chloride form. The enzyme activity was assayed under standard conditions.

EXAMPLE 1

Purification of Alkaline Phosphatase

When *T. neapolitana* cells were suspended in Buffer A and stirred gently for 1 h, some alkaline phosphatase was found in the supernatant. Enzyme extraction efficiency was increased in the presence of 0.15% Triton X-100. After two extractions with Triton X-100. Nearly all of the alkaline phosphatase was recovered in the supernatant. Table 1 summarizes the purification protocol and results of the purification of alkaline phosphatase from *T. neapolitana*.

The crude alkaline phosphatase obtained from the cell extraction was highly thermostable. When this crude alkaline phosphatase extract was heated at 100° C. for 40 min in the presence of 40 mM Co$^{2+}$, the residual activity was 97%, and the specific activity of the supernatant was increased 6.4 fold.

Interestingly, Co$^{2+}$ promoted strong affinity binding between the alkaline phosphatase and the ligand in the subsequent affinity chromatography step. In the absence of Co$^{2+}$, the alkaline phosphatase did not bind to the histidyl-diazobenzylpropionic acid-Agarose column even at pH value between 6 and 10 and room temperature. In the presence of Co$^{2+}$, most of the enzyme remained on the affinity column even after elution 1 M NaCl. (FIG. 1). The enzyme was totally eluted by 10 mM substrate such as p-nitrophenyl phosphate or 10 mM of an inhibitor such as potassium phosphate. The affinity chromatography step resulted in greater purification of the alkaline phosphatase (FIG. 1).

The native molecular weight of the protein was 87,000 estimated by gel filtration chromatography column indicating that the protein was homogenous dimer. The molecular weight was comparable to that of alkaline phosphatase from other microorganisms such as *E. coli* and *Bacillus subtilis* (McComb et al., supra).

Figure 2:
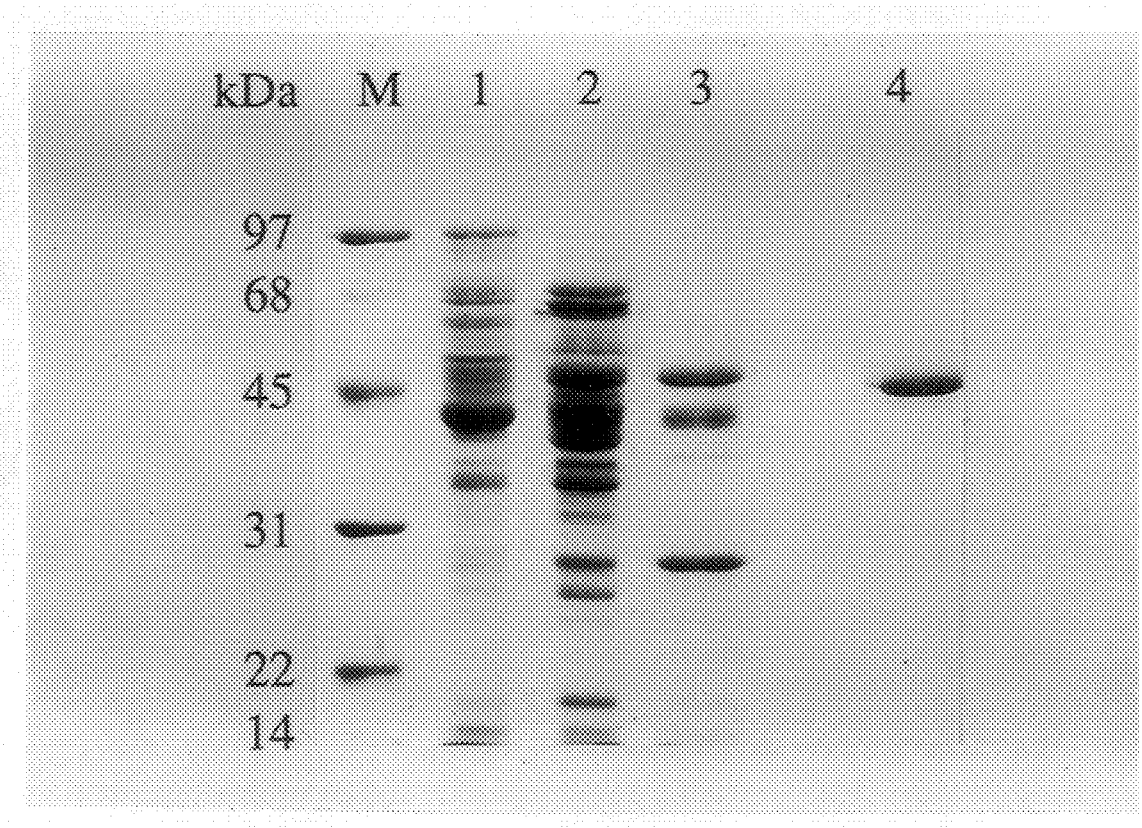
FIG. 2 is a SDS-PAGE (12%) pattern of *T. neapolitana* alkaline phosphatase. Lane M, marker proteins; lane 1, crude enzyme; lane 2, crude enzyme after treated at 100° C. in the presence of 40 mM cobalt ion; lane 3, the partially purified enzyme eluted from DEAE-Sepharose column; lane 4, purified protein from the affinity column.

FIG. 2 shows the SDS-Page pattern of samples at different purification steps. After the affinity chromatography step, the alkaline phosphatase displayed a single protein band on the electrophoresis gel with a subunit molecular weight of 45,000. The enzyme was purified 2880 fold with a yield of 44% overall (See Table 1).

TABLE 1

Summary of Purification of Protocol for the *T. neapolitana* Alkaline Phosphatase

| Stages | Total Activity (U) | Activity (U/ml) | Specific Activity (U/mg) | Yield (%) | Purification Fold |
|---|---|---|---|---|---|
| Initial | 321.0 | 1.6 | 0.23 | 100.0 | 1.0 |
| Heat Treatment | 345.9 | 12.4 | 1.42 | 110.9 | 6.2 |
| DEAE-Sepharose | 228.4 | 5.9 | 23.5 | 73.2 | 101.3 |
| Affinity column | 142.3 | 9.4 | 663.3 | 44.3 | 2882.6 |

The molecular weight of the native protein was 87,000 as estimated by gel filtration chromatography. In light of the SDS-PAGE results, the protein appears to be a homogeneous dimer. The molecular weight was very comparable to the molecular weight of the dimeric alkaline phosphatases from *Escherichia coli* and *Bacillus subtilis*. (See McComb et al., supra).

EXAMPLE 2

Figure 3A:
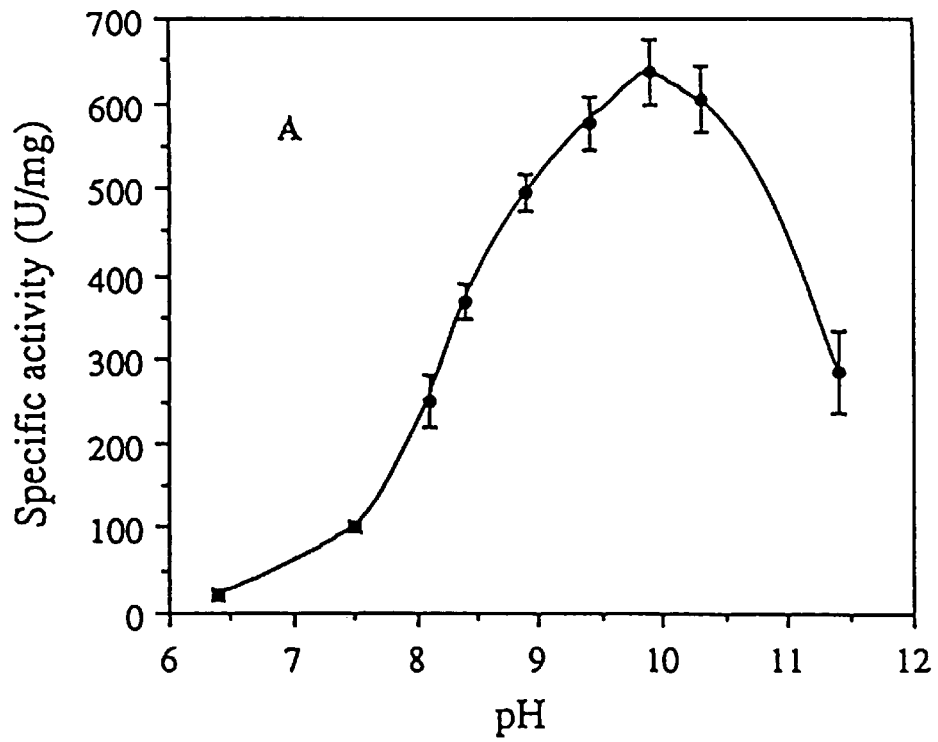
FIG. 3 shows *T. neapolitana* alkaline phosphatase activity as a function of pH and temperature. (A) The enzyme activity was measured at 60° C. in the 0.2 M Tris-HCl buffer at varying pHs. (B) the enzyme activity was detected at pH pH 9.9 under varying temperature.

Effect of pH and Temperature on *T. neapolitana* Alkaline Phosphatase Activity and Stability Like the alkaline phosphatase of *E. coli* and other alkaline phosphatases previously reported, *T. neapolitana* alkaline phosphatase activity increased with Tris concentration up to a plateau, starting at 0.2 M Tris. Thus, 0.2 M Tris was used for all the enzyme activity assays. FIG. 3A shows the alkaline phosphatase activity determined under different pH values at 60° C. The highest activity was obtained around pH 9.9. At neutral pH, the enzyme activity was significantly lower.

Figure 3B:
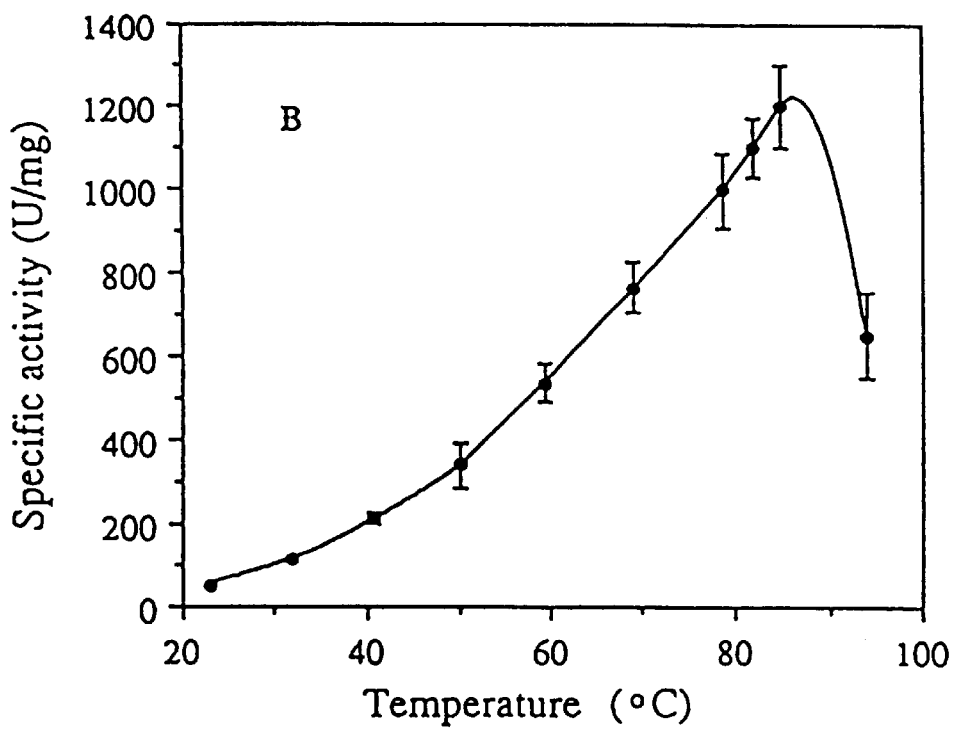

Because *T. neapolitana* grows at temperatures up to 90° C., the effect of temperature on the enzyme activity also was determined. As shown in FIG. 3B, the enzyme activity increased with increasing temperature from 20° C. to 85° C., and optimal activity was detected around 85° C.

The alkaline phosphatase was stable over a broad pH range (pH 4–11) when stored in Tris-HCl buffer at room temperature. It did not require anaerobic conditions for its stability. When stored at high temperatures, however, the enzyme became unstable at both lower and higher pH values. The enzyme displayed the highest stability at neutral pH.

Figure 4:
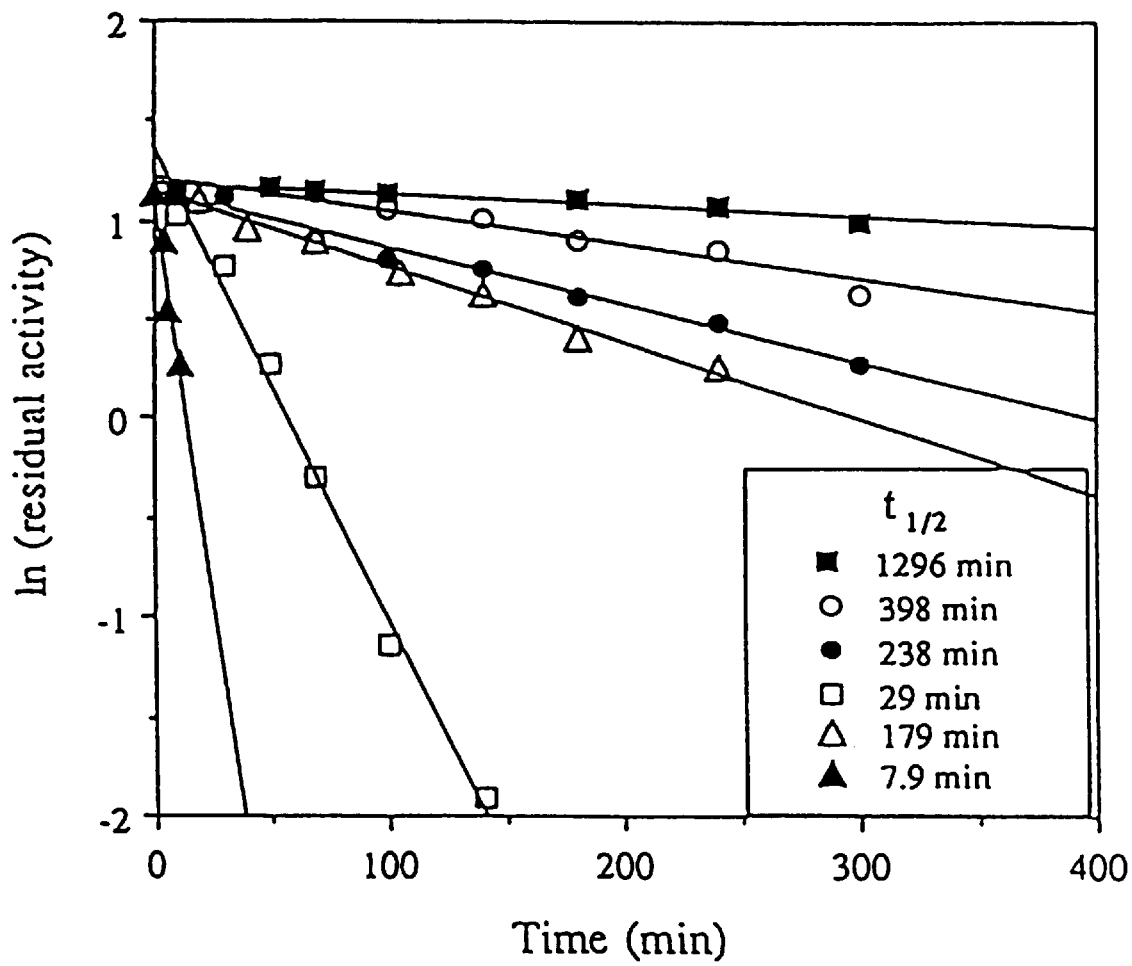
FIG. 4 depicts thermostability of *T. neapolitana* alkaline phosphatase at 60° C. (■), 80° C. (○), 90° C. (●, Δ, ▲) and 100° C. (□), respectively. Incubations were performed in the presence of $Co^{2+}$ (■, ○, ●, □), $Mg^{2+}$ (Δ), or without additional metal ion (▲). Half lives were calculated from the equation $t_{1/2}=\ln 2/K$ where the K is the thermoinactivation constant.

The thermostability of the *T. neapolitana* alkaline phosphatase increased 30 and 23 folds in the presence of Co$^{2+}$ or Mg$^{2+}$, respectively. (FIG. 4). The enzyme remains fully active at room temperature after 4 hours at pH 6.5–7.5. The enzyme was stable at 60° C. (half life of 21 h 30 min) or below. At 80° C. the enzyme has a half life of 6 h 40 min, but its activity was quickly lost above 90° C. (half life of 4 h at 90° C. and 30 min at 100° C.).

Table 2 compares the half lives of alkaline phosphatases from *T. neapolitana* and other sources under different temperature.

TABLE 2

Comparison of different alkaline phosphatase thermostabilities

| Sources | Temp. (°C.) | Metal ion added | Half life (min) | Reference |
|---|---|---|---|---|
| T. neapolitana | 90 | $Co^{2+}$ | 238 | present work |
| T. neapolitana | 90 | $Mg^{2+}$ | 179 | present work |
| T. neapolitana | 65 | $Co^{2+}$ | 1125 | present work |
| Control (calf intestine) | 65 | $Mg^{2+}$ | 60 | present work |
| Escherichia coli | 90 | $Mg^{2+}$ | 8 | 1 |
| Bacillus subtilis | 65 | $Mg^{2+}$ | 28 | 2 |
| Micrococcus sodonensis | 80 | $Ca^{2+}$ | 2 | 3 |
| Aspergillus nidulans | 70 | $Mg^{2+}$ | 8 | 4 |
| Kidney (Swine) | 57 | $Mg^{2+}$ | 12 | 5 |
| Osseous plates (Rat) | 55 | $Mg^{2+}$ | 9 | 6 |
| Neutrophile (Bovine) | 56 | $Mg^{2+}$ | 20 | 7 |

1 A. Garen et al., Biochem, Biophys. Acta, 38: 470–476 (1960).
2 A. R. Glenn et al., Biochem. J., 123: 129–138 (1971).
3 R. H. Glew et al., J. Biol. Chem., 246: 1566–1574 (1971).
4 G. L. Dorn et al., J. Biol. Chem., 243: 3500–3506 (1968).
5 E. D. Wachmuth et al., Biochem. J., 141: 273–282 (1974).
6 J. C. Say et al., Biochem. Biophys. Acta, 1074: 256–262 (1991).
7 S. Yasuura et al., Comp. Biochem. Physiol., 82B: 587–593 (1985).

The heat inactivation rate of any enzyme depends on the energy required to disrupt its native structure. This, in turn, is governed by such factors as the amino acid sequence, the degree of folding of the polypeptide chains, the presence of hydrophobic and other intramolecular bonds. Other factors that have been shown to influence thermal inactivity of enzyme include ionic strength, pH, substrate, and so on. To date, the limited information available concerning enzyme thermostability has arisen primarily from studies relating to mesophilic organisms. The present invention provides the opportunity to study, and to discover more information concerning, the mechanism behind enzyme thermostability.

EXAMPLE 3

Enzyme Kinetic Properties

*T. neapolitana* alkaline phosphatase kinetic properties were measured using p-nitrophenyl phosphate as a substrate. Under optimal temperature and pH conditions, the Km and Vmax, were $1.83 \times 10^{-4}$ M and 1352 U/mg, respectively.

*T. neapolitana* and calf intestine alkaline phosphatases hydrolyze a wide variety of phosphorylated compounds but display different specificities, as shown in Table 3. *T. neapolitana* alkaline phosphatase showed the highest activity when p-nitrophenyl phosphate was used as a substrate activity, whereas fructose-1,6-phosphate was more easily hydrolyzed by the alkaline phosphatase of calf intestine.

TABLE 3

Comparison of substrate specificity of alkaline phosphatase from *T. neapolitana* with that of commercial enzyme

| | Specific Activity of Alkaline Phosphatase (U/mg) | |
|---|---|---|
| Substrate | T. neapolitana[a] | Calf intestine[b] |
| p-Nitrophenyl-phosphate | 1309 | 926 |
| Adenosine 5'-diphosphate | 695 | 1072 |
| Adenosine 5'-triphosphate | 509 | 472 |
| Fructose-6-phosphate | 406 | 873 |
| Fructose-1,6-diphosphate | 696 | 1524 |
| Glucose-1-phosphate | 644 | 1180 |
| Glucose-6-phosphate | 457 | 1087 |
| Glycerophosphate | 825 | 1120 |

[a]Assay conditions were 0.2 M Tris (pH 9.9) at 80° C. in the presence of 5 mM $Co^{2+}$ and 5 mM $Mg^{2+}$.
[b]Assay conditions were 0.1 M Tris-HCl buffer (pH 8.5) at 38° C. in the presence of 50 mM $Mg^{2+}$ and 5 mM $Zn^2$

EXAMPLE 4

Effect of Metal Ions

*T. neapolitana* alkaline phosphatase was inactivated in the presence of EDTA. Only about 5% of its original activity was detected after exhaustive treatment with EDTA; the apoenzyme activity was regained upon the addition of divalent metal ions (Table 4).

The influence of metal ions on the apoenzyme activity was pronounced. Of all of the metal ions tested, $Co^{2+}$ has the most marked effect. While the presence of $Mg^{2+}$ ion, $Zn^{2+}$ ion, or $Mn^{2+}$ ion increases the apoenzyme activity about 18 times, up to 90–95% of the purified enzyme activity (663.3 U/mg) (measured in the absence of added salt), $Co^{2+}$ ion increases the enzyme activity almost 33 times to 163% of the specific activity of the purified enzyme (663.3 U/mg) (measured in the absence of added salt). $Cu^{2+}$ and $Ni^{2+}$ were inhibitors. (See Table 4).

Figure 5A:
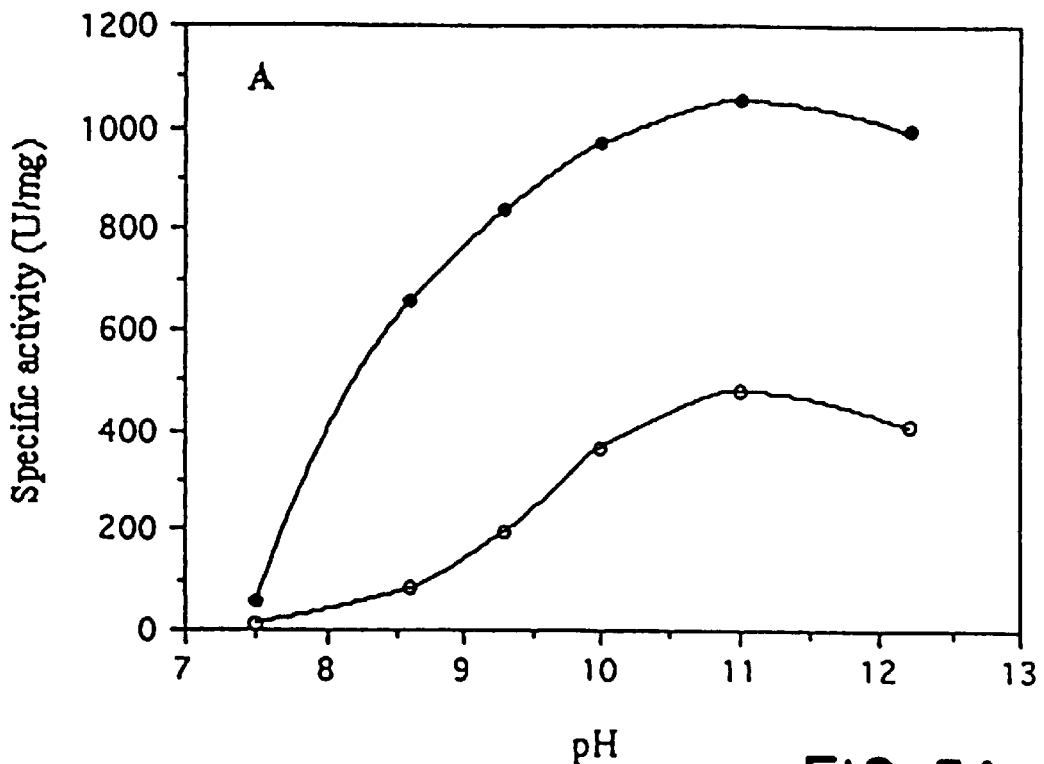
FIG. 5 illustrates the effect of pH and temperature on the apoenzyme activity in the presence of 2 mM $Zn^{2+}$ ion (○) or 2 mM $Co^{2+}$ ion (●) respectively. (A) The enzyme activity was measured in 0.2 M Tris-HCl buffer at different pHs and a constant temperature of 60° C. (B) The enzyme activity was detected at pH 9.9 at different temperatures.
Figure 5B:
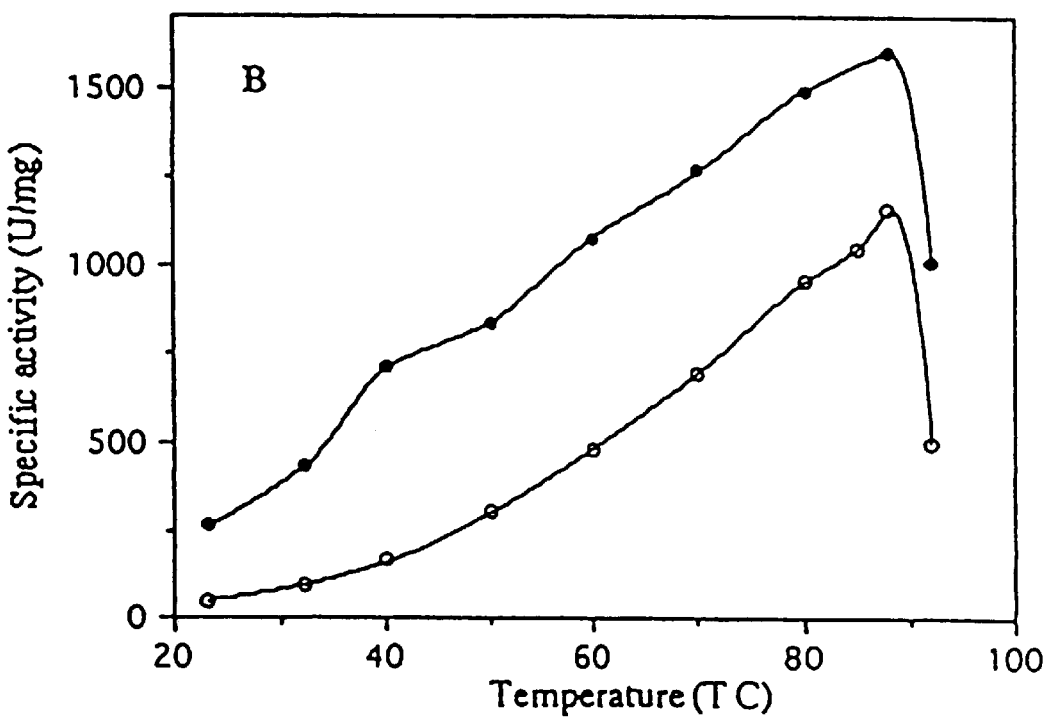

The effects of pH and temperature on the activities of the *T. neapolitana* apoenzyme treated with 2 mM $Co^{2+}$ or $Zn^{2+}$ also were examined (FIG. 5). The apoenzyme in the presence of $Zn^{2+}$ had almost identical optimal pH and temperature activity profiles as the untreated *T. neapolitana* alkaline phosphatase (See FIG. 3). However, $Co^{2+}$ had a very favorable effect on the apoenzyme activity. After treatment with $Co^{2+}$ ion, the apoenzyme activity was increased 7.7 times at room temperature and neutral pH compared to untreated enzyme or enzyme treated in the presence of $Zn^{2+}$, and its optimal pH range broadened. These results suggest that the $Co^{2+}$ ion made the reaction site more active and/or changed the conformation of the enzyme's active site which, in turn, increased the affinity between the protein and its ligand.

TABLE 4

Effect of metal ions on *T. neapolitana* apoenzyme activity

| Metal ion | Specific activity (U/mg) |
|---|---|
| Control (no metal ion) | 33.2 |
| $Co^{2+} + Mg^{2+}$ | 1128 |
| $Co^{2+}$ | 1085 |

TABLE 4-continued

Effect of metal ions on *T. neapolitana* apoenzyme activity

| Metal ion | Specific activity (U/mg) |
|---|---|
| $Mg^{2+}$ | 594 |
| $Zn^{2+}$ | 582 |
| $Mn^{2+}$ | 591 |
| $Ca^{2+}$ | 460 |
| $Ba^{2+}$ | 428 |
| $Sr^{2+}$ | 499 |
| $Ni^{2+}$ | 207 |
| $Cu^{2+}$ | 73 |

The contents of all the references cited herein above are incorporated herein by reference.

One skilled in the art will appreciate from a reading of this disclosure that various changes in form and detail can be made without departing from the true scope of this invention.

We claim:

1. A thermostable alkaline phosphatase isolated from *Thermotoga neapolitana* DSM 5068.

2. The alkaline phosphatase according to claim 1, having the following chemical properties:
   (1) Molecular weight: approximately 87,000;
   (2) Activator: $Co^{2+}$;
   (3) optimum temperature: 85° C.;
   (4) pH stability at room temperature: 5.0–11.5 (for residual activity equal or above 95%;
   (5) pH optimum: 9.9;
   (6) $K_m$ and $V_{max}$ values of 183 μM and 1352 U/mg respectively.

3. A process for preparing a hyperthermostable alkaline phosphatase comprising the steps of:
   preparing a cell culture of the bacterium *T. neapolitana* (DSM 5068);
   isolating the enzyme alkaline phosphatase from said cell culture of said bacterium by heat treatment in the presence of $Co^{2+}$, and
   purifying the isolated enzyme using a combination of ion exchange and affinity chromatographies.

4. The process of claim 3 wherein said heat treatment step comprises applying heat treatment at 100° C.

5. A process for producing alkaline phosphatase from *Thermotoga neapolitana* DSM 5068 comprising the steps of:
   preparing an cell extract from *Thermotoga neapolitana* DSM 5068;
   applying heat to the cell extract in the presence of a divalent metal ion;
   rapidly cooling the cell extract;
   applying centrifugal force to the cell extract and discarding the resultant precipitate;
   adding ammonium sulfate to the resultant soluble reaction;
   harvesting the resultant pellet by centrifugation then resuspending said pellet in a buffer having a relatively neutral pH and subjecting the resulting solution to dialysis;
   applying the dialyzed solution to an ion-exchange resin under conditions such that said alkaline phosphatase binds to said resin;
   separating said bound alkaline phosphatase from unbound materials present in said solution;
   eluting said alkaline phosphatase from said resin whereby a partially purified alkaline phosphatase is obtained.

6. The process of claim 5 wherein said divalent metal ion is $Co^{2+}$.

7. The process according to claim 7, further comprising the step of subjecting said partially purified alkaline phosphatase to affinity chromatography and eluting said alkaline phosphatase by pulse elution whereby purified alkaline phosphatase is obtained, and wherein the resultant alkaline phosphatase has an optimum pH of 9.9 and an optimum temperature of about 85° C.

* * * * *